(12) United States Patent
Griffith et al.

(10) Patent No.: US 11,612,732 B2
(45) Date of Patent: Mar. 28, 2023

(54) ENTERAL FEEDING DEVICE CONNECTOR

(71) Applicant: Avent, Inc., Alpharetta, GA (US)

(72) Inventors: Nathan Griffith, Johns Creek, GA (US); Donald McMichael, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 136 days.

(21) Appl. No.: 16/084,753

(22) PCT Filed: Mar. 18, 2016

(86) PCT No.: PCT/US2016/023076
§ 371 (c)(1),
(2) Date: Sep. 13, 2018

(87) PCT Pub. No.: WO2017/160308
PCT Pub. Date: Sep. 21, 2017

(65) Prior Publication Data
US 2019/0070403 A1 Mar. 7, 2019

(51) Int. Cl.
*A61M 39/12* (2006.01)
*A61J 15/00* (2006.01)
*A61M 39/10* (2006.01)

(52) U.S. Cl.
CPC .......... *A61M 39/12* (2013.01); *A61J 15/0026* (2013.01); *A61M 2039/1033* (2013.01);
(Continued)

(58) Field of Classification Search
CPC ........ A61J 15/0026; A61M 2039/1033; A61M 2039/1077; A61M 2039/1083;
(Continued)

(56) References Cited

U.S. PATENT DOCUMENTS

| 4,211,439 A | * | 7/1980 | Moldestad | ............ | F16L 37/113 |
| | | | | | 285/376 |
| 5,399,173 A | * | 3/1995 | Parks | .................. | A61J 15/0026 |
| | | | | | 16/2.1 |

(Continued)

FOREIGN PATENT DOCUMENTS

| CN | 201520469 U | 7/2010 |
| CN | 203737179 U | 7/2014 |

(Continued)

OTHER PUBLICATIONS

International Search Report and Written Opinion for PCT/US2016/023076, dated Nov. 21, 2016, 11 pages.

*Primary Examiner* — Shefali D Patel
(74) *Attorney, Agent, or Firm* — Dority & Manning, P.A.

(57) ABSTRACT

An enteral feeding adapter suitable for use with a plurality of infusion sets includes an outer body component made of a flexible material and containing a feeding port for receipt of a distal connector of an infusion set. A rigid body insert is seated within an internal recess of the outer body component and defines a proximal section of the feeding port. The insert includes a first continuous radial seal barb that engages the flexible material of the outer body component, and a plurality of separate and circumferentially spaced radial second seal barbs distal to the first seal barb that engage the flexible material.

16 Claims, 5 Drawing Sheets

(52) U.S. Cl.
CPC ............... *A61M 2039/1077* (2013.01); *A61M 2039/1083* (2013.01); *A61M 2039/1088* (2013.01)

(58) Field of Classification Search
CPC .......... A61M 2039/1088; A61M 39/12; A61M 2202/0482; A61M 39/08; A61M 39/10; A61M 2039/085
See application file for complete search history.

(56) References Cited

U.S. PATENT DOCUMENTS

| | | | |
|---|---|---|---|
| 5,569,222 A | | 10/1996 | Haselhorst et al. |
| 5,988,700 A | * | 11/1999 | Prichard ............... A61M 39/10 285/148.23 |
| 5,997,503 A | | 12/1999 | Willis et al. |
| 5,997,546 A | | 12/1999 | Foster et al. |
| 6,019,746 A | | 2/2000 | Picha et al. |
| 6,808,521 B1 | * | 10/2004 | McMichael ......... A61J 15/0026 285/148.23 |
| 2005/0033268 A1 | | 2/2005 | Decaria |
| 2008/0140055 A1 | | 6/2008 | Shirley |
| 2015/0032089 A1 | | 1/2015 | Way |
| 2016/0206516 A1 | | 7/2016 | Kunishige et al. |

FOREIGN PATENT DOCUMENTS

| | | |
|---|---|---|
| CN | 203868565 U | 10/2014 |
| JP | 2015188521 A | 11/2015 |

\* cited by examiner

ENTERAL FEEDING DEVICE CONNECTOR

CROSS-REFERENCED TO RELATED APPLICATIONS

This application is a national phase of and claims priority to PCT/US2016/023076, filed Mar. 18, 2016, the contents of which are incorporated herein by reference hereto.

FIELD OF THE INVENTION

The present invention relates generally to the field of enteral feeding devices, and more specifically to a connector component of such devices configured for receipt of an infusion feeding tube.

BACKGROUND OF THE INVENTION

It is a known medical procedure to catheterize a body in order to provide nutritional solutions directly into the stomach or intestines of a patient. A stoma is formed in the stomach or intestinal wall and a catheter is placed through the stoma. Feeding solutions can be injected through a catheter inserted in the stoma to provide nutrients directly to the stomach or intestines. This process is referred to in the medical field as "enteral feeding", and various designs of commercially available enteral feeding devices are well-known and understood by those skilled in the art, including the MIC™ GJ standard feeding tube and MIC-KEY™ GJ low profile feeding tube from Halyard Health, Inc., having a principal place of business at Alpharetta, Ga., U.S.A.

FIG. 1 is a perspective view of a commercially available MIC™ GJ standard feeding tube device 4, and FIG. 2 is an enlarged view of the feeding adapter component 6 of the device. Referring particularly to FIG. 2, the adapter component defines a jejunal feeding port 8, a separate gastric feeding port 10, and a medicine injection port 12, and is made of a relatively soft or flexible medical grade material. Each port 6, 8 includes a plurality of internal ribs 14 molded therein for frictional connection with the distal end of an infusion set tube inserted into the respective port to prevent the tube from being dislodged or pulled from the adapter port.

With the conventional enteral feeding devices, to ensure that the catheter is maintained in the proper position, it is common to use a balloon disposed near the distal end of the catheter shaft. Inflating the balloon causes the balloon to contact the anatomical structure (i.e., a duct or stomach wall) and thereby prevent the catheter from moving out of the proper position. Such balloon catheter devices may include a "low-profile" head at the proximal end of the catheter shaft. The head, which also helps hold the balloon catheter in place, includes an opening for receiving the feeding solution and a one-way valve for preventing fluids from passing out of the patient via the catheter. U.S. Pat. Nos. 5,997,503 and 5,997,546 disclose examples of low-profile balloon catheters suitable for enteral feeding.

Because feeding solutions must be fed through the relatively small head of the balloon catheter located atop the patient's skin, an enteral feeding adapter is used to transfer the solutions from a source to the catheter. Such adapters typically include an elongate feeding tube having connecting elements on each end thereof. On the distal end of the tube, one of the connecting elements engages the head of the balloon catheter to place the tube in communication with the catheter. The proximal end of the tube typically includes another connecting element in the form of an adapter body for receiving the distal end of an infusion set, and also possibly a syringe for use in inflating the balloon component. The infusion set, in turn, may be connected to an enteral feeding pump, a drip chamber, or any other mechanism for providing a feeding solution.

An issue with available enteral feeding adapters is that the adapter bodies are typically configured specifically for use with a particular infusion set of a given diameter and configuration. Most of the commercially available infusion sets, however, are not of a standardized size or configuration. For example, infusion sets marketed by various companies have widely different distal end configurations. Some have substantially cylindrical surfaces at the infusion set distal end, and some have substantially tapered surfaces at this location for push-in connection. Even with the tapered end configuration, while the infusion set distal end might be received by an adapter designed for a different sized infusion set, the engagement would be so loose that the distal end could easily be pulled from the adapter. Thus, infusion sets and the adapters are generally not interchangeable.

The need for a universal small-bore connector standard for medical devices has been emphasized by the Association for the Advancement of Medical Instrumentation (AAMI) and, in 2009, manufacturers, clinicians, and regulators (including the U.S. Food and Drug Administration) collaborated with the Internal Organization for Standardization (ISO) and the AAMI or development of a new standard known as ISO 80369-3 standard for enteral feeding tube applications. Under this standard, feeding tube adapters will utilize a Luer connection specifically standardized for enteral feeding applications.

The current standard of "push-in" style tapered connectors between the infusion set distal end and enteral feeding adapter typically uses a flexible material interface. This will not suffice for a Luer-style connector, and a rigid material interface must be designed for this purpose under ISO 80369-3 standard that still interfaces with the relatively soft tubing that is implanted in the patient. This new interface must effectively seal to prevent leakage of stomach contents and feeding solution, and must also resist rotational and linear forces that are generally necessary to establish a connection.

Accordingly, the present invention addresses the need for a new enteral feeding adapter that affixes one or more rigid connectors (e.g., suitable for a Luer connector) to flexible tubing containing one or more lumens with a robust seal and resistance to rotational and liner forces.

SUMMARY OF THE INVENTION

Objects and advantages of the invention will be set forth in the following description, or may be obvious from the description, or may be learned through practice of the invention.

For purposes of this disclosure, the term "distal" refers to a direction closest to the patient, and the term "proximal" refers to a direction closes to the clinician when the enteral feeding device is used as intended.

In accordance with aspects of the invention, an enteral feeding adapter is provided for use in delivering substances into a patient. Although not limited to such use in all embodiments, the enteral feeding adapter is particularly suitable for use with a plurality of infusion sets (e.g. infusion sets from different suppliers or manufacturers) having distal screw-on type connectors, such as standardized Luer connectors.

The enteral feeding adapter includes an outer body component made of a relatively soft or flexible material containing a feeding port configured for receiving a distal connector of an infusion set, with the feeding port defining an internal recess within the outer body component. A rigid body insert is seated within the internal recess of the outer body component and includes an internal passage that defines a proximal section of the feeding port. The rigid body insert includes a first radial seal barb that extends continuously around the circumference of the rigid body and engages the flexible material of the outer body component. The rigid body insert further includes a plurality of separate and circumferentially spaced second seal barbs distal to the first seal barb. These separate second seal barbs also have a radial component that engages the flexible material of the outer body component.

The internal recess of the outer body member in which the rigid body insert is seated has a reduced geometry that is sized to create an interference fit with the first and second seal barbs upon insertion of the rigid body insert into the outer body component to create a sealed interface between the outer body component and the rigid body insert. For example, the internal recess of the outer body member has a first geometry with radial spaces that generally conforms to a "shrunken" shape of the rigid body insert with reduced radial dimensions, wherein this first geometry radially expands (and may also expand axially to some extent) upon insertion of the rigid body insert into the internal recess.

In a particular embodiment, the individual second seal barbs have the same radial and circumferential dimensions, and further include a gap between adjacent second seal barbs. The gaps may be defined such that the second seal barbs are equally spaced around the circumference of the rigid body insert. In an alternate embodiment, the gaps are defined and located so that the second seal barbs are not equally spaced around the circumference of the rigid body component. For example, the gaps may have different circumferential lengths or radial depths, or both. The spaces within the internal recess of the outer body member are correspondingly shaped and spaced. With this type of embodiment, insertion of the rigid body insert necessarily must occur at a defined orientation in order for the second seal barbs to properly engage and seal within their respective spaces in the internal recess of the outer body member.

In a certain embodiment, the second seal barbs are axially elongated and have a proximal end spaced from the first seal barb and a distal end that extends to a distal end of the rigid body component. The second seal barbs may also taper in the radial dimension from the proximal end to a distal end thereof.

The feeding port defined in the enteral feeding adapter includes an internal tube extending distally within the outer body component from a distal end of the rigid body insert. In one embodiment, this tube is a structure directly molded into the material of the outer body component. In another embodiment, this tube may be a component that is formed separately from the outer body component, with the outer body component molded around the separately formed tube.

In still another embodiment, the rigid body insert may include a connection head that extends proximally beyond a proximal end of the outer body component, with this head further including a fitting for connection to an infusion set. This fitting may be, for example, a Luer screw-on fitting.

It should be appreciated that the enteral feeding adapter is not limited to a particular number of feeding or other type of ports. For example, the enteral feeding adapter may include a medicine injection port configured in the outer body for injection of medication through the enteral feeding adapter. Still further, the adapter may include a second one of the feeding ports configured in the outer body for receipt of a second infusion set. For example, one of the feeding ports may be a jejunal feeding port, and a second one of the feeding ports may be a gastric feeding port, as in understood in the art.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Figure 1:
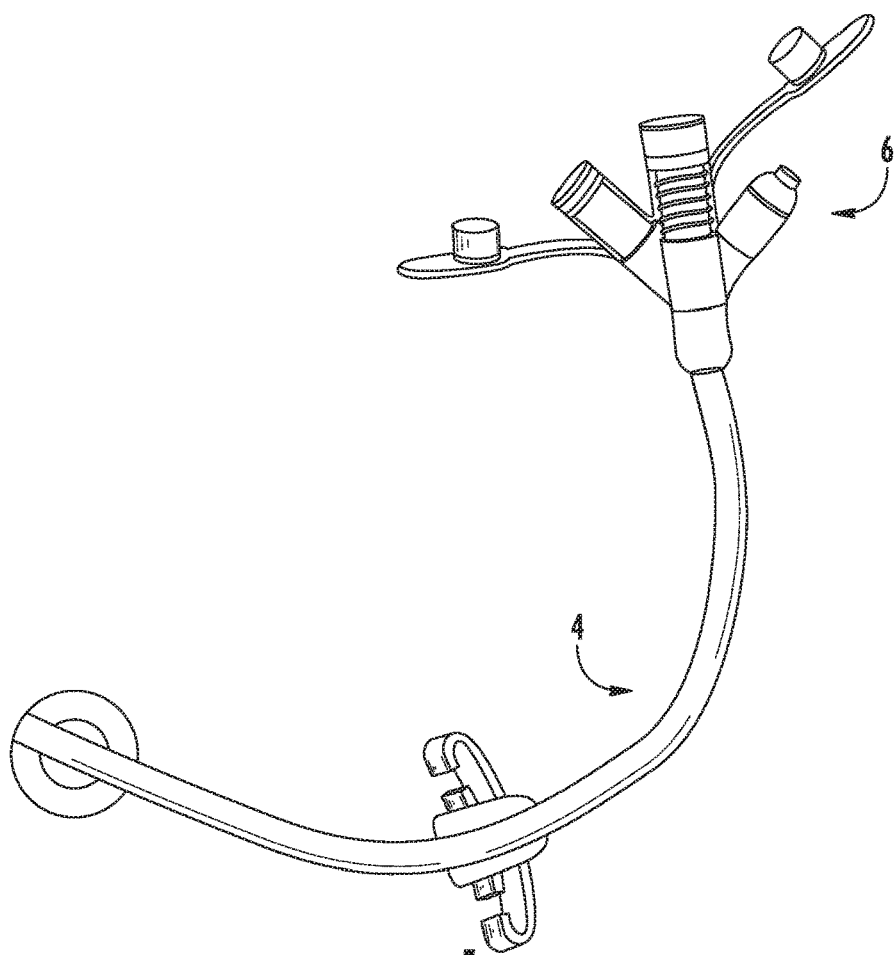
FIG. 1 is a perspective view of a prior art enteral feeding device.
Figure 2:
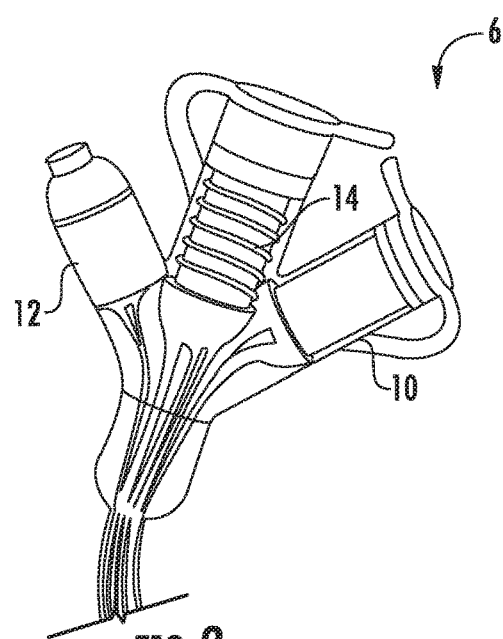
FIG. 2 is a perspective view of the adapter component of the enteral feeding device of FIG. 1.
Figure 3:
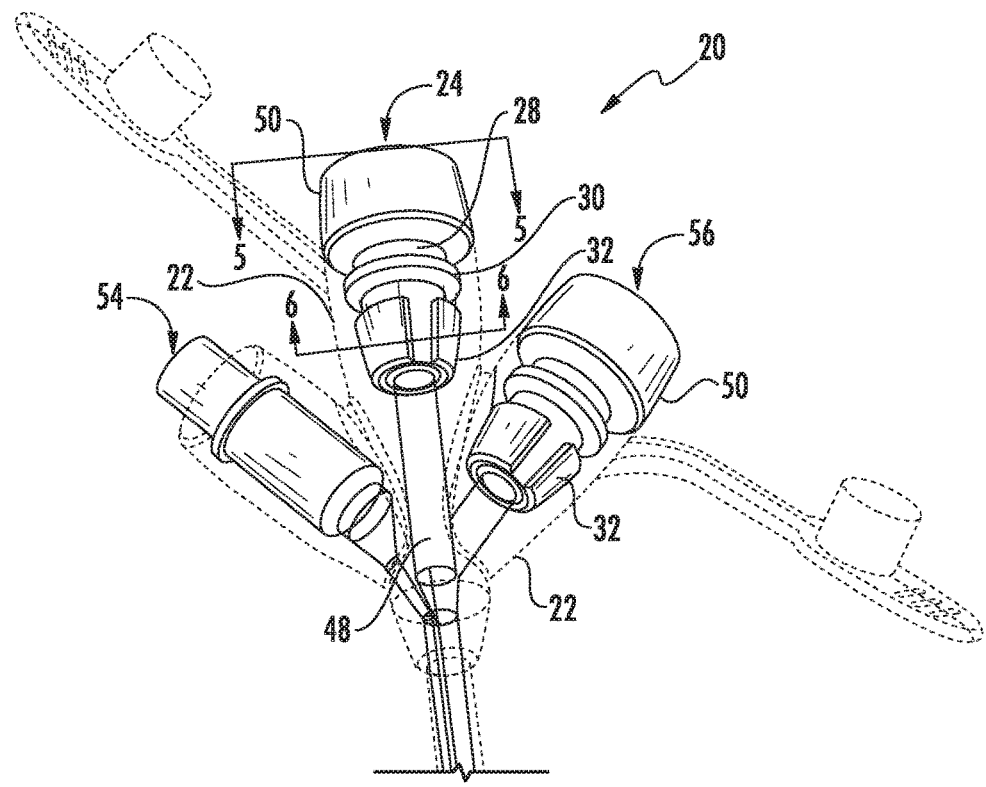
FIG. 3 is a perspective view of an enteral feeding adapter in accordance with aspects of the invention.

Referring to FIG. 3, an enteral feeding adapter 20 in accordance with aspects of the invention is provided for use in delivering substances into a patient. The enteral feeding adapter is suitable for use with a plurality of different infusion sets, particularly infusion sets having a standardized Luer fitting 58 (FIG. 5) to connect a feeding tube 60 to a distal end of the adapter 20.

Still referring to FIG. 3, the feeding adapter 20 includes an outer body component 22 made of a soft or flexible material. Such materials are known and used in the industry, and may include any one of number of commercially available medical grade polymers, such a medical grade silicone or PVC material. The outer body component 20 contains a feeding port 24 configured for receiving the distal connector 58 of an infusion set.

Figure 5:
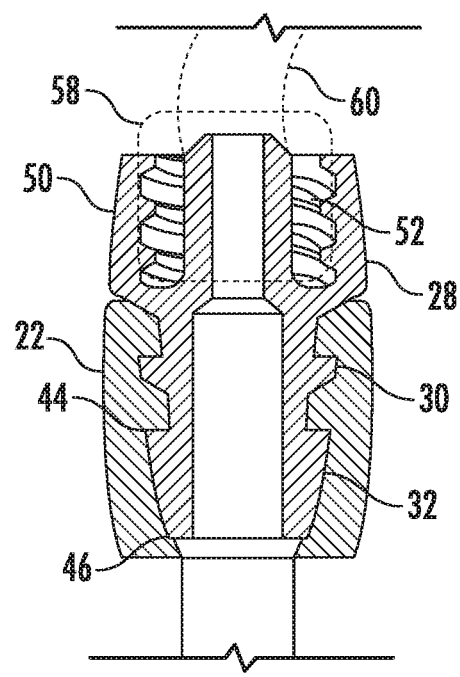
FIG. 5 is a longitudinal cross-sectional view of the enteral feeding adapter of FIG. 3 taken along the lines indicated.
Figure 6:
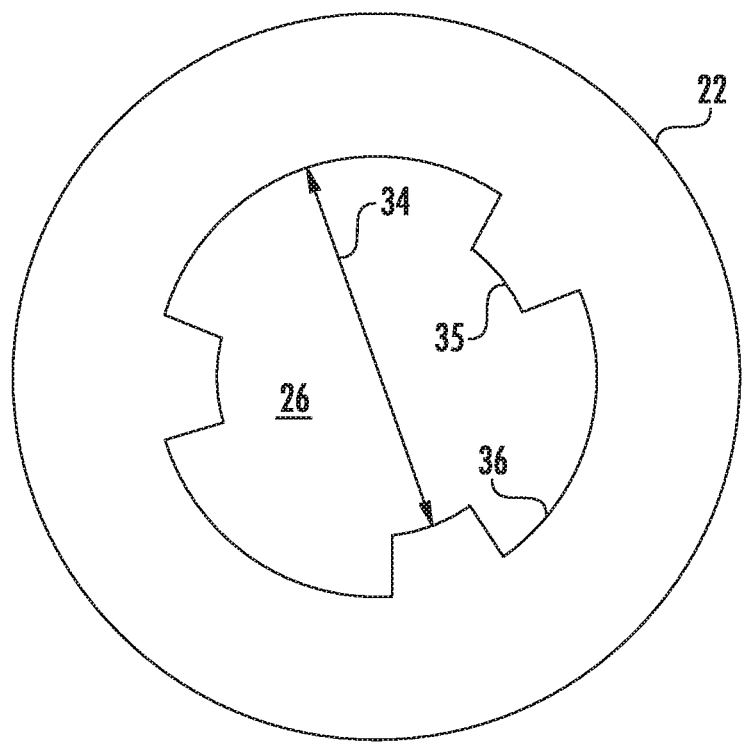
FIG. 6 is a radial cross-sectional view of the enteral feeding adapter of FIG. 3 taken along the lines indicated.
Figure 7:
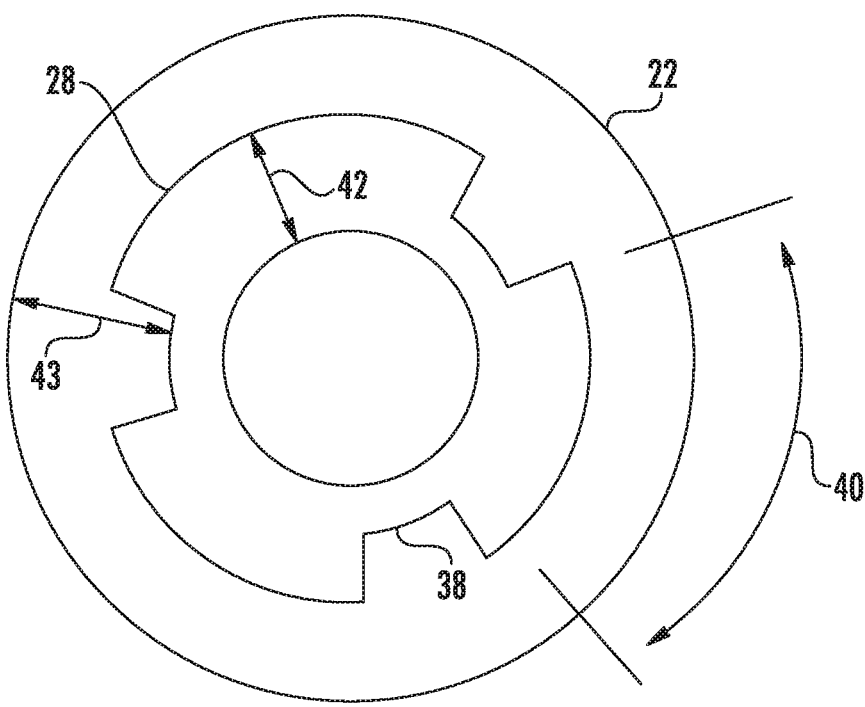
FIG. 7 is a radial cross-sectional view of an alternate embodiment of an enteral feeding adapter.

The outer body component 22 includes an internal recess 26 (FIG. 6) in which a rigid body insert 28 is seated, as particularly depicted in FIGS. 5 and 7. This insert 28 may be a molded plastic component that retains its rigidity and shape once inserted into the internal recess 26. In this regard, the outer body component 22 is "flexible" or "soft" to the degree that it is able to stretch and conform to the outer dimensions of the rigid body insert 28 and form a frictional seal therewith around the circumference of the rigid body insert 28. The rigid body insert 28 has an internal passage that defines the proximal section of the feeding port 24, as can be seen in FIG. 5.

Referring particularly to FIGS. 3 and 5 through 7, the rigid body insert 28 has a proximal fitting section 50 that may extend proximally beyond the proximal end of the outer body component 22, as depicted in the figures. In another embodiment, the proximal fitting section 50 may be encased within the outer body component 22. Spaced from the fitting section 50, is a first radial seal barb 30 that extends continuously around the circumference of the rigid body insert 28 and engages and seals with the flexible material of the outer body component 22, as particularly seen in FIG. 5.

As seen in FIGS. 3 and 5, the rigid body insert 28 further includes a plurality of separate and circumferentially spaced second seal barbs 32 spaced distally from the first seal barb 30 that also engage and seal with the flexible material of the outer body component 22. In the embodiment depicted in FIGS. 5 and 7, the second seal barbs have a radial dimension 42 that may be the same for all of the barbs 32. Alternately, the barbs 32 may have different radial dimensions 42. The barbs are separated in the circumferential direction by gaps 38. In the depicted embodiments, these gaps 38 have a varying size such that the barbs 32 are not spaced equally around the circumference of the rigid body insert 28. In addition, the gaps 38 have a radial depth 43 that may also vary between different gaps 38, as depicted in FIG. 7. Each barb 38 also has a circumferential dimension 40 that may be uniform among the barbs (depicted in the various figures), or may vary between different barbs 32.

FIG. 6 is a cross-sectional view of the outer body component 22 in a "relaxed" state before insertion of the rigid body insert 28. The internal recess 26 has a reduced geometry 34 compared to the rigid body insert 28 that is sized to create an interference fit with the first 30 and second 32 seal barbs upon insertion of the rigid body insert 28 into the outer body component 22 to create a sealed interface between the outer body component 22 and the rigid body insert 28. For example, it can be appreciated from FIG. 6 that spaces 36 intended to accommodate the barbs 32 will expand radially outward upon insertion of the barbs 32 therein, while the projections 35 engage into the gaps 38 between the barbs 32. FIG. 7 shows the rigid body insert 28 inserted within the recess 26 and illustrates these structural relationships.

As seen in FIG. 5, the second seal barbs 32 have an axial dimension defined between a proximal end 44 and a distal end 46, wherein the distal end 46 may extend to a distal end of the rigid body inert 28. In this embodiment, the second seal barbs 32 may taper in the radial dimension from the proximal end 44 to the distal end 46, as depicted in FIG. 5.

The feeding port 24 in the enteral feeding adapter 20 includes an internal tube 48 extending distally from a distal end of the rigid body insert 28, as seen in FIG. 3. In one embodiment, this internal tube is a molded feature of the outer body component. In an embodiment depicted in the figures, the internal tube 48 is a tube formed separately from the outer body component 22, with the outer body component 22 molded around the separately formed tube 48. The tube 48 mates with the distal end of the rigid body insert 28.

As mentioned, in the depicted embodiments, the rigid body insert 28 includes a connection head 50 that extends proximally beyond a proximal end of the outer body component 22, wherein this connection head 50 includes a fitting 52 for connection to an infusion set. This fitting 52 may be a male or female component of a conventional Luer screw-on fitting that has been standardized for enteral feeding devices.

Figure 4:
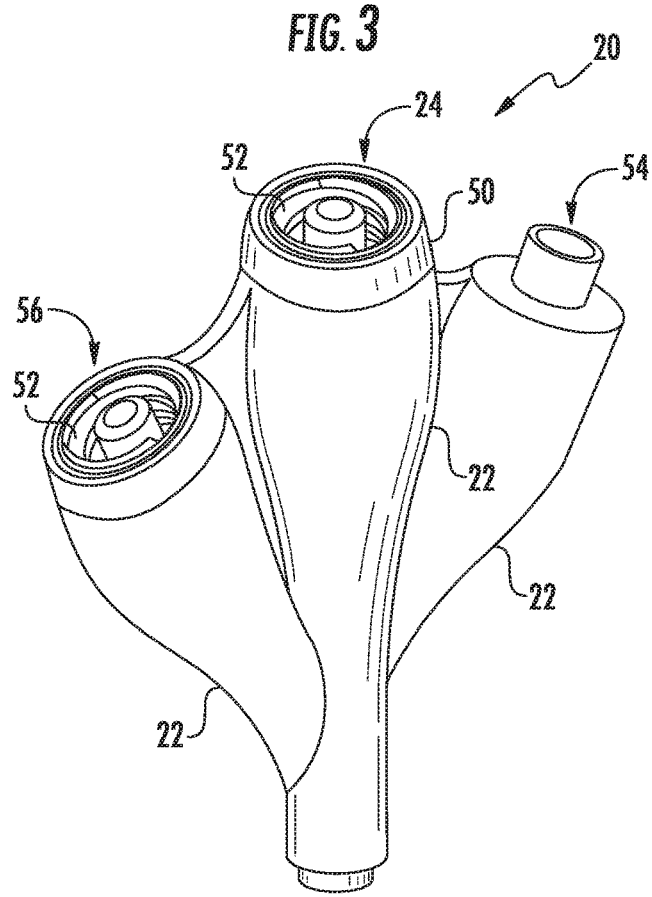
FIG. 4 is a top-end perspective view of an enteral feeding adapter in accordance with aspects of the invention.
Figure 8:
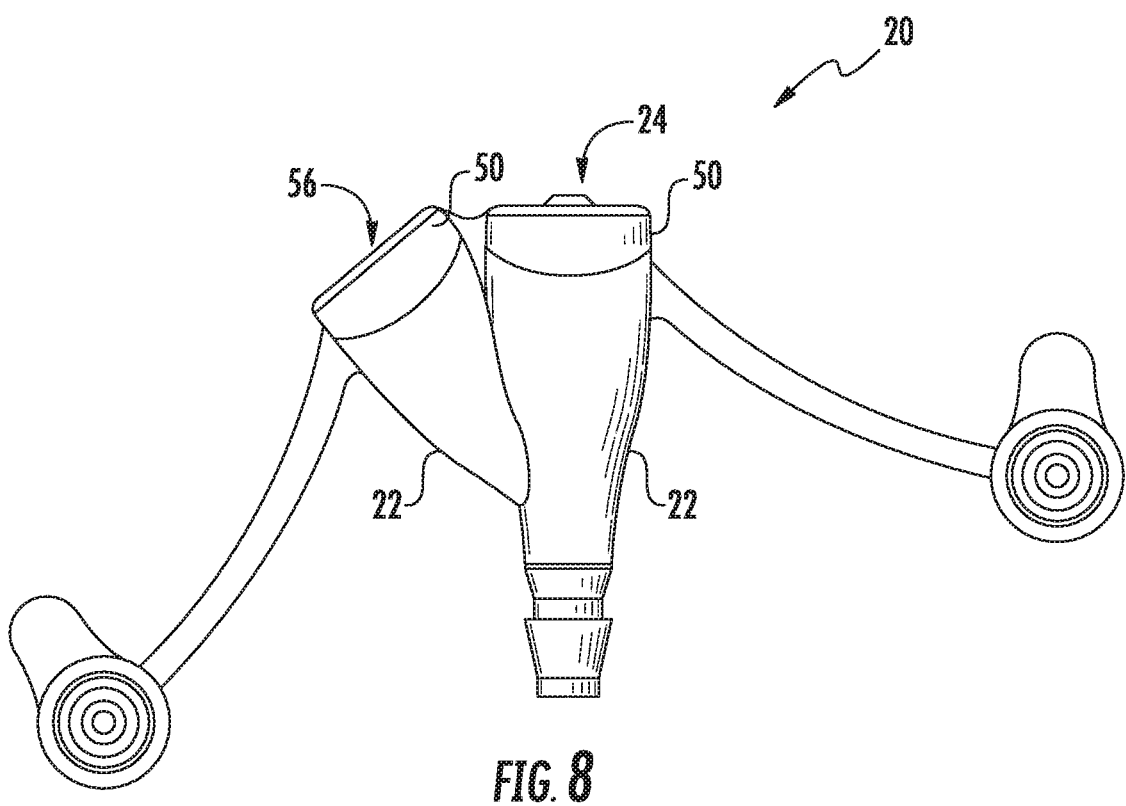
FIG. 8 is a side perspective view of an alternate embodiment of an enteral feeding adapter.
Figure 9:
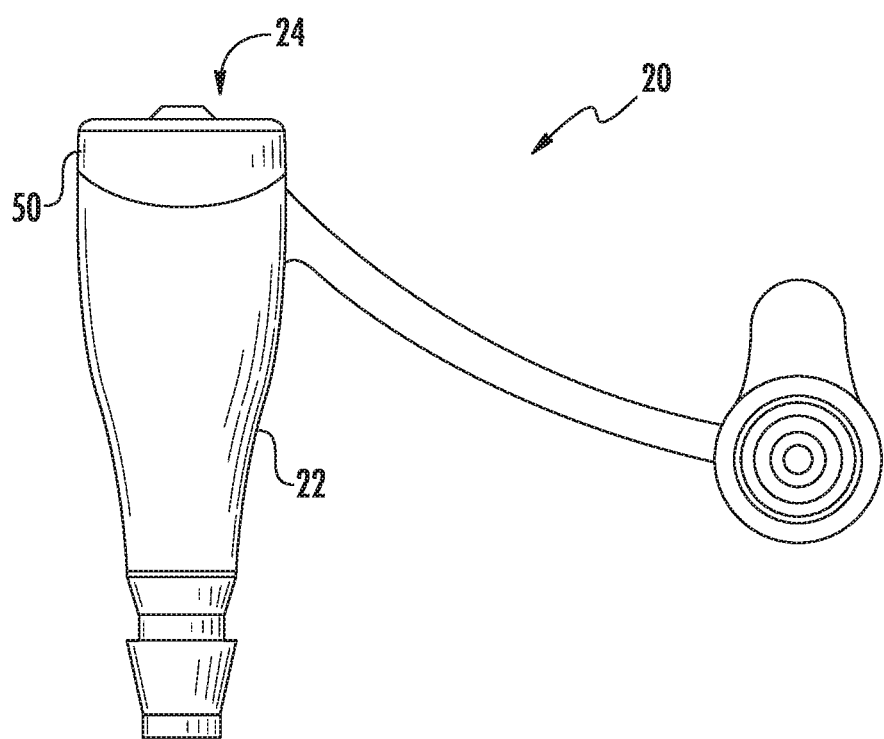
FIG. 9 is a side perspective view of still another embodiment of an enteral feeding adapter.

It should be appreciated that aspects of the present invention may be incorporated with multiple ports on the same enteral feeding adapter 20. FIG. 9 depicts an embodiment of an adapter 20 having a single feeding port 24 as described herein. FIG. 8 depicts an embodiment of an adapter 20 having an additional feeding port 56. For example, the first port 24 may be a jejunal feeding port, and the second port 56 may be a gastric feeding port. In still another embodiment depicted in FIG. 4, the adapter 20 may include a medicine injection port 54. Adapters 20 having multiple feeding ports and/or a medicine injection port are known and used in the art, and need not be described in detail herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An enteral feeding adapter for use in delivering substances into a patient, the enteral feeding adapter suitable for use with a plurality of infusion sets having distal screw-on type connectors, the enteral feeding adapter comprising:

an outer body component made of a flexible material containing a feeding port configured for receiving a distal connector of an infusion set, the feeding port defining an internal recess, wherein the feeding port further comprises an internal tube extending distally within the outer body component from a distal end of a rigid body insert;

the rigid body insert seated within the internal recess of the feeding port of the outer body component and defining a proximal section of the feeding port;

the rigid body insert further comprising a fitting section, wherein the fitting section extends proximally beyond a proximal end of the outer body component;

the rigid body insert further comprising a first continuous radial seal barb that engages the flexible material of the outer body component;

the rigid body insert further comprising a plurality of separate and circumferentially spaced radial second seal barbs distal to the first seal barb that engage the flexible material, wherein gaps are present between adjacent second seal barbs of the plurality of second seal barbs; and the internal recess of the feeding port of the outer body component having a reduced geometry that is sized to create an interference fit with the first seal barb and the second seal barbs upon insertion of the rigid body insert into the outer body component to create a sealed interface between the outer body component and the rigid body insert, wherein the first seal barb is located adjacent a proximal end of the rigid body insert, further wherein the internal recess of the feeding port of the outer body component comprises spaces and projections to accommodate the second seal barbs, wherein the spaces and the projections extend to a position at which the internal tube is received in the outer body component, wherein the second seal barbs are located adjacent the distal end of the rigid body insert, wherein the second seal barbs are in contact with the spaces and the projections when the rigid body insert is fully seated into the outer body component, and wherein the projections are separated from each other in a circumferential dimension by the spaces.

2. The enteral feeding adapter as in claim 1, wherein the internal recess of the feeding port of the outer body component has a first geometry that conforms to a shape of the rigid body insert with reduced radial dimensions, wherein the first geometry radially expands upon insertion of the rigid body insert into the internal recess.

3. The enteral feeding adapter as in claim 1, wherein the second seal barbs have a same radial and circumferential dimension.

4. The enteral feeding adapter as in claim 1, wherein the gaps are defined such that the second seal barbs are not equally spaced around a circumference of the rigid body insert.

5. The enteral feeding adapter as in claim 1, wherein the second seal barbs have a proximal end spaced from the first seal barb and a distal end that extends to the distal end of the rigid body insert.

6. The enteral feeding adapter as in claim 5, wherein the second seal barbs taper in a radial dimension from the proximal end to the distal end thereof.

7. The enteral feeding adapter as in claim 1, wherein the internal tube is a molded structure of the outer body component.

8. The enteral feeding adapter as in claim 1, wherein the internal tube is a tube formed separately from the outer body component, with the outer body component molded around the separately formed tube.

9. The enteral feeding adapter as in claim 1, wherein the fitting section further comprises a fitting for connection to the infusion set.

10. The enteral feeding adapter as in claim 9, wherein the fitting comprises a Luer screw-on fitting.

11. The enteral feeding adapter as in claim 1, further comprising an injection port configured in the outer body component for injection of a medication through the enteral feeding adapter.

12. The enteral feeding adapter as in claim 1, further comprising a second one of the feeding port configured in the outer body component for receipt of a second infusion set.

13. The enteral feeding adapter as in claim 1, wherein the second seal barbs have varying circumferential dimensions.

14. The enteral feeding adapter as in claim 1, wherein the first seal barb has a proximal end and a distal end spaced from the fitting section of the rigid body insert.

15. The enteral feeding adapter as in claim 14, wherein the first seal barb tapers in a radial dimension from the proximal end to the distal end thereof.

16. The enteral feeding adapter as in claim 1, wherein the gaps are not all of equal size in one or both of a radial dimension or the circumferential dimension.

\* \* \* \* \*